United States Patent
Weiss et al.

(10) Patent No.: US 8,911,940 B2
(45) Date of Patent: Dec. 16, 2014

(54) METHODS OF ASSESSING A RISK OF CANCER PROGRESSION

(75) Inventors: Glen Weiss, Phoenix, AZ (US); Seungchan Kim, Phoenix, AZ (US); Sara Nasser, Phoenix, AZ (US)

(73) Assignees: The Translational Genomics Research Institute, Phoenix, AZ (US); Scottsdale Healthcare Corporation, Scottsdale, AZ (US)

( * ) Notice: Subject to any disclaimer, the term of this patent is extended or adjusted under 35 U.S.C. 154(b) by 153 days.

(21) Appl. No.: 13/387,997

(22) PCT Filed: Jul. 29, 2010

(86) PCT No.: PCT/US2010/043777
§ 371 (c)(1),
(2), (4) Date: Mar. 28, 2012

(87) PCT Pub. No.: WO2011/014697
PCT Pub. Date: Feb. 3, 2011

(65) Prior Publication Data
US 2012/0178093 A1 Jul. 12, 2012

Related U.S. Application Data

(60) Provisional application No. 61/230,402, filed on Jul. 31, 2009, provisional application No. 61/347,171, filed on May 21, 2010.

(51) Int. Cl.
*C12Q 1/68* (2006.01)
*C12P 19/34* (2006.01)

(52) U.S. Cl.
USPC .......................... 435/6.1; 435/6.12; 435/91.2

(58) Field of Classification Search
USPC ........................................ 435/6.1, 6.12, 91.2
See application file for complete search history.

(56) References Cited

U.S. PATENT DOCUMENTS

| | | | | |
|---|---|---|---|---|
| 7,575,863 | B2 * | 8/2009 | Chen et al. | 435/6.12 |
| 7,772,389 | B2 * | 8/2010 | Tuschl et al. | 536/24.5 |
| 2005/0261218 | A1 | 11/2005 | Esau et al. | |
| 2006/0019258 | A1 | 1/2006 | Yeakley et al. | |
| 2007/0015176 | A1 | 1/2007 | Lao et al. | |
| 2007/0092882 | A1 | 4/2007 | Wang et al. | |
| 2008/0050744 | A1 | 2/2008 | Brown et al. | |
| 2008/0306018 | A1 | 12/2008 | Croce et al. | |
| 2009/0105174 | A1 | 4/2009 | Jayasena | |
| 2009/0275039 | A1 | 11/2009 | Moser et al. | |
| 2010/0233704 | A1 | 9/2010 | Michot et al. | |

FOREIGN PATENT DOCUMENTS

| | | |
|---|---|---|
| WO | 2006/069584 | 7/2006 |
| WO | 2007/081720 | 7/2007 |
| WO | 2007/148235 | 12/2007 |

OTHER PUBLICATIONS

Gaur et al., "Characterization of MicroRNA Expression Levels and Their Biological Correlates in Human Cancer Cell Lines", Cancer Res., 67(6):2456-2468 (Mar. 15, 2007).
Na et al., "A diagnostic model to detect silent brain metastases in patients with non-small cell lung cancer", European Journal of Cancer, 44(16):2411-2417 (Nov. 1, 2008).
Nass et al., "MiR-92b and miR-9/9* are Specifically Expressed in Brain Primary Tumors and can be Used to Differentiate Primary from Metastatic Brain Tumors", Brain Pathology, 19(3):375-383 (Jul. 2009).
Nasser et al., "Identifying MiRNA and Imaging Features Associated with Metastasis of Lung Cancer to the Brain", BIBM, pp. 346-351, 2009 IEEE International Conference on Bioinformatics and Biomedicine, Nov. 1-4, 2009.
Pang et al., "Oncogenic role of microRNAs in brain tumors", Acta Neuropathol., 117(6):599-611 (Jun. 2009).
Raponi et al., "MicroRNA Classifiers for Predicting Prognosis of Squamous Cell Lung Cancer", Cancer Research, 69(14):5776-5783 (Jul. 2009).
Saad et al., "Immunohistochemical markers associated with brain metastases in patients with nonsmall cell lung carcinoma", Cancer, 113(8):2129-2138 (Oct. 15, 2008).
Schmittgen et al., "Real-time PCR quantification of precursor and mature microRNA", Methods, 44:31-38 (2008).
Wang et al., "MicroRNA miR-328 Regulates Zonation Morphogenesis by Targeting CD44 Expression", PLOS ONE, 3(6):1-14 (Jun. 1, 2008).
Wang et al., "Potential Uses of MicroRNA in Lung Cancer Diagnosis, Prognosis, and Therapy", Current Cancer Drug Targets, 9(4):572-594 (Jun. 2009).
European Search Report for corresponding European Patent Application No. 10805072.5 dated Oct. 24, 2012.
International Search Report and Written Opinion of the International Searching Authority for PCT/US2010/043777 dated Oct. 25, 2010.
International Preliminary Report on Patentability for PCT/US2010/043777 dated Feb. 9, 2012.
Russel A. H. et al., Prophylactic Cranial Irradiation for Lung Cancer Patients at High Risk for Development of Cerebral Metastasis: Results of a Prospective Randomized Trial Conducted by the Radiation Therapy Oncology Group, Int. J. Radiation Oncology Biol. Phys., 1991, pp. 637-643, vol. 21, No. 3.
Potgen C. et al., The role of prophylactic cranial irradiation in the treatment of lung cancer, Lung Cancer, 2001, pp. S153-S158, 33 Suppl. 1.
Patel N. et al., Prophylactic crainal irradiation for preventing brain metastases in patients undergoin radical treatment for non-small cell lung cancer, Cochrane Database of Systematic Reviews, 2005, pp. 1-15, Issue 2.
Paumier A. et al., Prophylactic cranial irradiation in lung cancer, Cancer Treatment Reviews, 2011, pp. 261-265 vol. 37.
Stuschke M. et al., Prophylactic cranial irradiation as a component of intensified initial treatment of locally advanced non-small cell lung cancer, Lung Cancer, 2003, pp. S53-S56, 42.

(Continued)

*Primary Examiner* — Ardin Marschel
(74) *Attorney, Agent, or Firm* — Rodney J. Fuller; Booth Udall Fuller PLC

(57) ABSTRACT

Methods and kits that use miRNA expression to predict the development of brain metastases in non-small cell lung cancer patients are disclosed.

10 Claims, 8 Drawing Sheets

(56) References Cited

OTHER PUBLICATIONS

Cox J. D. et al., Cranial Irradiation in Cancer of the Lung of All Cell Types, The Journal of the American Medical Association, 1981, pp. 469-472, vol. 245, No. 5.

Gore E. et al., Non-small Cell Lung Cancer and Central Nervous System Metastases: Should We Be Using Prophylactic Cranial Irradiation?, Seminars in Radiation Oncology, 2004, pp. 292-297, vol. 14.

Lester J. F. et al., Prophylactic Cranial Irradiation for Preventing Brain Metastases in Patients Undergoing Radical Treatment for Non-Small-Cell Lung Cancer: A Chochrane Review, Int. J. Radiation Oncology Biol. Phys., 2005, pp. 690-694, vol. 63, No. 3.

Stuschke M. et al., Prophylactic Cranial Irradiation in Locally Advanced Non-Small-Cell Lung Cancer After Multimodality Treatment: Long-Term Follow-Up and Investigations of Late Neuropsychologic Effects, Journal of Clinical Oncology, 1999, pp. 2700, 2709, vol. 17.

Chi A., Treatment of Brain Metastasis from Lung Cancer, Cancers, 2010, pp. 2100-2137, vol. 2.

Pugh T J. et al., Prophylactic Cranial Irradiation for Patients with Lung Cancer, Clinical Lung Cancer, 2007, pp. 365-368, vol. 8, No. 6.

\* cited by examiner

*p =0.0265
p =0.00869

US 8,911,940 B2

METHODS OF ASSESSING A RISK OF CANCER PROGRESSION

RELATED APPLICATION DATA

This application is the U.S. National Stage of International Application No. PCT/US10/43777, filed Jul. 29, 2010, which claims priority to U.S. Provisional Patent Application No. 61/230,402, filed Jul. 31, 2009 and U.S. Provisional Patent Application No. 61/347,171, filed May 21, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,745 byte ASCII (text) file named "Seq_List" created on Jan. 30, 2012.

BACKGROUND OF THE INVENTION

In 2009, an estimated 219,000 cases of lung cancer were diagnosed in the US (See Reference 1) It is the leading cause of cancer deaths and ~80% of patients with primary lung malignancy have non-small cell lung cancer (NSCLC). Brain metastasis (BM) can affect up to 25% of these patients during their lifetime (See Reference 2). BM cause significant neurologic, cognitive, and emotional difficulties (See Reference 3) and negatively impact survival (See Reference 4). Previous efforts to characterize patients that will develop BM have been disappointing. Currently, prophylactic cranial irradiation (PCI) is offered to all small cell lung cancer patients (but not to NSCLC patients) with early-stage disease that have responded to therapy or have stable disease after initial systemic treatment (See Reference 5). However, better selection of patients to offer PCI will spare those patients unlikely to develop BM from PCI-related side effects. Currently, there are no common practice measures to reduce the risk of BM in NSCLC. In locally-advanced stage III NSCLC, a clinical trial to determine the benefit of PCI accrued slowly and the study was terminated early, and is therefore, not statistically powered to meet the primary endpoint of improvement in survival (See Reference 6). Thus, there is a need for improvement in patient stratification. Molecular biomarkers could be of benefit to stratify these patients, but the ability to obtain adequate, quality tumor tissue in a standardized fashion for genomic profiling can be challenging and hence limiting. Recently, microRNAs (miRNAs) have been studied to characterize tumors (See Reference 7). miRNAs are small non-coding RNAs of 21-25 nucleotides that may act as molecular biomarkers. Due to their influence on cell physiology, alteration of miRNA regulation can be implicated in carcinogenesis and disease progression. In general, one miRNA appears to regulate several hundred genes, and as a result, miRNA profiling could serve as a better classifier than gene expression profiling (See Reference 8).

BRIEF SUMMARY OF THE INVENTION

The present invention provides among other things: a method of predicting recurrence of non-small cell lung cancer.

It is an object of the invention to identify lung cancer patients with an increased risk of brain metastasis.

It is an object of the invention to provide a blood test that identifies which lung cancer patients are likely to develop brain metastases.

The above and other objects may be achieved through the use of methods involving obtaining a serum sample from a subject and isolating RNA from the sample, adding a first reagent capable of specific binding to a marker that includes a sequence selected from the group consisting of SEQ ID NO. 1 and SEQ ID NO. 2 to a mixture comprising the sample and subjecting the mixture to conditions that allow detection of the binding of the first reagent to the marker wherein the cohort comprises two or more individuals with small cell lung cancer likely to develop brain metastases. The first reagent may comprise a first oligonucleotide such as a stem-loop oligonucleotide. The method may further comprise adding reverse transcriptase and subjecting the mixture to conditions that comprise allowing the formation of a DNA template comprising the marker. The method may further comprise adding a second oligonucleotide and a third oligonucleotide to the mixture. The second oligonucleotide and the third oligonucleotide bind to opposite strands of the DNA template. For example, if the second oligonucleotide binds to the 5'→3' strand, then the third oligonucleotide binds to the 3'→5' strand. The method may further comprise adding a fourth oligonucleotide to the mixture. The fourth oligonucleotide binds to the DNA template between the sequences to which the second oligonucleotide and the third oligonucleotide are capable of binding. The fourth oligonucleotide may comprise a label. The label may be any label including a fluorescent label such as FAM, dR110, 5-FAM, 6FAM, dR6G, JOE, HEX, VIC, TET, dTAMRA, TAMRA, NED, dROX, PET, BHQ, Gold540, or LIZ. Alternatively, the conditions may comprise DNA sequencing. The first reagent may be affixed to a substrate. The sample may be any sample including a sample comprising serum or a lung biopsy. The method may also include collecting the sample from the subject. The above and other objects may be achieved through the use of kits comprising a first reagent capable of specific binding to a marker that includes a sequence selected from the group consisting of SEQ ID NO. 1 and SEQ ID NO. 2 and an indication of a result that signifies classification of the subject into a cohort. The first reagent may comprise a first oligonucleotide such as a stem loop oligonucleotide. The kit may further comprise a second oligonucleotide and a third oligonucleotide wherein the second oligonucleotide and the third oligonucleotide are capable of binding to opposite strands of a DNA construct comprising the reverse transcription product of the marker. For example, if the second oligonucleotide binds to the 5'→3' strand, then the third oligonucleotide binds to the 3'→5' strand. The kit may further comprise a fourth oligonucleotide capable of binding to a sequence between the sequences to which the second oligonucleotide and the third oligonucleotide are capable of binding. The fourth oligonucleotide may comprise a label, including a fluorescent label such as FAM, dR110, 5-FAM, 6FAM, dR6G, JOE, HEX, VIC, TET, dTAMRA, TAMRA, NED, dROX, PET, or LIZ. The kit may also comprise an enzyme such as a DNA polymerase, (including, for example, a thermostable DNA polymerase) or a reverse transcriptase. Alternatively, the first reagent may be affixed to a substrate. The kit may further comprise a device to be used in collecting a sample. The result may comprise a $\Delta Ct$ value. The result may alternatively comprise a nucleic acid sequence listing. The indication may comprise a positive control. Alternatively, the indication may comprise a writing that may be physically included in the kit, may be made available via a website, may comprise an amplification plot, or may comprise a photograph. Alternatively, the indication may comprise software configured to detect the result as input and classification of the subject into the cohort as output. The software may be incorporated into any machine including a machine configured to detect fluorescence.

BRIEF DESCRIPTION OF THE FIGURES

A more complete understanding of the present invention may be derived by referring to the detailed description when considered in connection with the following illustrative figures.

Figure 1:
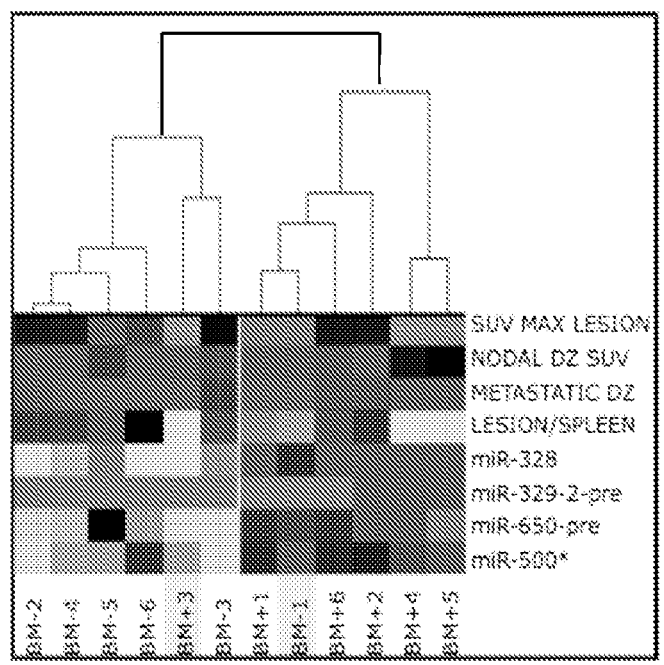
FIG. 1 depicts hierarchical clustering of samples with features selected via rank correlation.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived or any other chemical structure. Examples of such nucleic acids include miRNA, tRNA, siRNA, mRNA, cDNA, or genomic DNA sequences including complimentary sequences. Modified nucleic acids such as methylated nucleic acids may also serve as markers. A marker may be represented by a protein sequence including posttranscriptional modifications such as phosphorylation. The concept of a marker is not limited to the products of the exact nucleic acid sequence or protein sequence by which it may be represented. Rather, a marker encompasses all molecules that may be detected by a reagent used in assessing the expression of the marker.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A reagent capable of binding to a sequence having less than 60% 70%, 80%, 90%, 95%, 99% or 100% identity to the identifying sequence may still be encompassed by the invention if it is still capable of binding to its complimentary sequence and/or facilitating nucleic acid amplification of a desired target sequence. If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence.

Examples of molecules encompassed by a marker represented by a particular sequence or structure include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following non-limiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moeties to proteins, phosphorylation, protein complex formation and any other process along a continuum that results in the production of biological material derived from a nucleic acid of particular sequence whether in vitro, in vivo, or ex vivo. Expression also encompasses all processes through which the production of biological material derived from a nucleic acid template may be actively or passively suppressed. Such processes include all aspects of transcriptional and translational regulation. Examples include heterochromatic silencing, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, nucleic acid amplification followed by nucleic acid sequencing, sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay or any method that uses a protein reagent, nucleic acid reagent, or other reagent capable of specifically binding to or otherwise recognizing a specific nucleic acid or protein marker.

Other methods used to assess expression include the use of such natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)2, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent,) stain, enzyme, metal, or any other substance capable of aiding a machine configured to detect a label or a human eye to identify differential expression of a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, by aided or unaided human eye, or any other method that may detect differential expression. Examples include but are not limited to differential staining of cells in an IHC assay configured to detect a marker, differential detection of bound RNA on a microarray to which a sequence capable of binding to the marker is bound, differential results in measuring RTPCR measured in ACt or alternatively in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular cellular or physiological characteristic. The level of expression may be derived from a single control or a set of controls. A control may be any sample with a previously determined level of expression. A control may comprise material within the sample or material from sources other than the sample. The expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic. A set of controls may be used to generate a standard curve to which the expression of the sample may be compared. This may allow a quantitative value to be placed on expression.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other disease outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than $1,000,000\times$, $100,000\times$, $10,000\times$, $1000\times$, $100\times$, $10\times$, $5\times$, $2\times$, $1\times$, $0.5\times$, $0.1\times$ $0.01\times$, $0.001\times$, $0.0001\times$, $0.00001\times$, $0.000001\times$ or less than that of a level predetermined to predict the presence or absence of a cellular or physiological characteristic.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic (as in a control) may be assessed by any of a number of methods. The skilled artisan will understand that numerous methods may be used to select a level of expression for a particular marker or a plurality of markers that signifies a particular physiological or cellular characteristic. In diagnosing the presence of a disease, a threshold value may be obtained by performing the assay method on samples obtained from a cohort of subjects known to have a certain type of disease (cancer for example,) and from a second cohort known not to have the disease. In assessing disease outcome or the effect of treatment, a population of subjects, all of whom have a disease such as cancer, may be followed for a period of time. After the period of time expires, the population may be divided into two or more cohorts. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the subject from which the sample was derived may be assigned to the cohort of subjects with the same level of expression and therefore may be predicted to have the same outcome as the subjects in that cohort.

Determining a level of expression that signifies a particular physiological or cellular characteristic may be achieved by any of a number of methods. For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982) hereby incorporated by reference.

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up. A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups; a value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into. One skilled in the art would recognize which method to select based on the type of expression, type of data, and physical or cellular characteristic that is signified by the expression.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

A subject includes any human or non-human animal, including for example: a primate, cow, horse, pig, sheep, goat, dog, cat, or rodent, capable of developing cancer including human patients that are suspected of having cancer, that have been diagnosed with cancer, or are likely to develop cancer. Methods of identifying subjects suspected of having cancer or that have been diagnosed with cancer include but are not limited to: physical examination, endometrial biopsy, or a number of imaging technologies such as ultrasonography, computed tomography, magnetic resonance imaging, magnetic resonance spectroscopy, or positron emission tomography. Methods of identifying subjects likely to develop cancer include analyses of family medical history, subject medical history, and genomic or other marker analysis.

Cancer comprises any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

In some aspects of the invention, the cancer comprises non-small cell lung cancer (NSCLC.) NSCLC includes any carcinoma derived from lung tissues that does not include small cell lung cancers. Examples of non-small cell lung cancers include adenocarcinomas, large cell carcinomas, and squamous cell carcinomas of the lung.

Metastasis is the spread of cancer, in which cancer cells move from the primary tumor and enter the blood stream or lymphatic system, spreading the cancer to different parts of the body. The cells in the metastatic tumor come from the original tumor, thus lung cancer that spreads to the brain will be made up of lung cancer cells and is also known as brain metastasis. More than 50% of brain metastasis is associated with SCLC and NSCLC. Brain is the major site of relapse, with 25% of NSCLC patients being affected by brain metastasis.

Upon diagnosis of NSCLC, imaging including CT Scan is used for staging and treatment planning CT scan may be performed on the chest, abdomen, and/or brain to examine for both the primary tumor and extent of metastatic cancer including the brain. Positron emission tomography (PET) scanning is a specialized imaging technique that uses short-lived radioactive drugs to produce three-dimensional colored images of those substances in the tissues within the body. While CT scans and MRI scans look at anatomical structures, PET scans measure metabolic activity and tissue activity including but not limited to tissue growth. CT, MRI, and PET scanning can yield a variety of datapoints well-known to those skilled in the art.

Treatment of lung cancer may include but need not be limited to surgical removal of the cancer, chemotherapy, or radiation therapy, as well as combinations of these treatments. Lung cancer patients with brain metastasis are primarily offered radiation treatment.

The present invention further provides kits to be used in assessing the expression of RNA in a subject to assess the risk of developing disease. Kits include any combination of components that may facilitate the performance of an assay. A kit that facilitates assessing the expression of RNA may include suitable nucleic acid-based and immunological reagents as well as suitable buffers, control reagents, and printed protocols.

Kits that facilitate nucleic acid based methods may include one or more of the following: specific nucleic acids such as oligonucleotides, labeling reagents, labels, enzymes including PCR amplification reagents such as Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker. Examples of labels include but are not limited to: a radioactive isotope or chelate thereof, a dye (fluorescent or nonfluorescent,) stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in expression analysis such as quantitative reverse transcriptase PCR. Examples of such dyes include but are not limited to: FAM, dR110, 5-FAM, 6FAM, dR6G, JOE, HEX, VIC, TET, dTAMRA, TAMRA, NED, dROX, PET, BHQ, Gold540, and LIZ.

An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and storage conditions, assume a two- or three-dimensional structure such as with a stem-loop oligonucleotide. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or affixed directly to a solid substrate as in oligonucleotide arrays among other things.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the case of a Southern Blot, Northern blot or other method that affixes the sample to a substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a result that signifies a particular physiological or cellular characteristic. An indication includes any result that, using the kit in which the indication is provided, would signal the presence or absence of any physiological or cellular state that the kit is configured to detect. The type of indication would vary based on the components of the kit and the method of using the kit to produce a result. The indication may be expressed numerically, expressed as a color, expressed as an intensity of a band, derived from a standard curve, or may comprise a control to which the result from the sample is compared. The indication may also include a DNA, RNA or protein sequence. The indication may be printed on a writing that may be included in the kit or it may be posted on the Internet or embedded in a software package. The writing may contain any printed material capable of communicating the indication such as a photograph, a chart, a graph, or any written description including a biological molecule sequence.

MicroRNA has been shown to be a major new class biomolecules involved in control of gene expression. For example, in human heart, liver or brain, miRNA play a role in tissue specification or cell lineage decisions. In addition, miRNAs influence a variety of processes, including early development, cell proliferation and cell death, and apoptosis and fat metabolism. The large number of miRNA genes, the diverse expression patterns and the abundance of potential miRNA targets suggest that miRNAs may be a significant but unrecognized source of human genetic disease. Differences in miRNA expression have also been found to be associated with cancer diagnosis, prognosis, and susceptibility to treatments.

A mature miRNA is typically an 18-25 nucleotide noncoding RNA that regulates expression of mRNA including sequences complementary to the miRNA. These small RNA molecules are known to control gene expression by regulating the stability and/or translation of mRNAs. For example, miRNAs bind to the 3' UTR of target mRNAs and suppress translation. MiRNA's may also bind to target mRNAs and mediate gene silencing through the RNAi pathway. MiRNAs may also regulate gene expression by causing chromatin condensation.

Endogenously expressed miRNAs are processed by endonucleolytic cleavage from larger double-stranded RNA precursor molecules. The resulting small single-stranded miRNAs are incorporated into a multiprotein complex, termed RISC. The small RNA in RISC provides sequence information that is used to guide the RNA-protein complex to its target RNA molecules. The degree of complimentarity between the small RNA and its target determines the fate of the bound mRNA. Perfect pairing induces target RNA cleavage, as is the case for siRNAs and most plant miRNAs. In comparison, the imperfect pairing in the central part of the duplex leads to a block in translation.

MicroRNAs regulate various biological functions including developmental processes, developmental timing, cell proliferation, neuronal gene expression and cell fate, apoptosis, tissue growth, viral pathogenesis, brain morphogenesis, muscle differentiation, stem cell division and progression of human diseases. Many miRNAs are conserved in sequence and function between distantly related organisms. However, condition-specific, time-specific, and individual-specific levels of gene expression may be due to the interactions of different miRNAs which lead to genetic expression of various traits. The large number of miRNA genes, the diverse expression patterns and the abundance of potential miRNA targets suggest that miRNAs may be a significant but unrecognized source of human genetic diseases. MicroRNA genetic alterations, such as deletion, insertion, reversion or conversion, may affect the accuracy of miRNA related gene regulation. MicroRNA genetic alterations may be used as markers for disease prognosis and diagnosis. MiRNA alleles may alternatively be used as target for disease treatment, and markers for disease prognosis and diagnosis. Common methods of analyzing miRNA such as array-based methods are unable to detect mutated miRNA.

MiRNA is readily detectable in blood and blood compartments such as serum or plasma or whole blood by any of a number of methods. See, for example, Chen X et al, *Cell Research* 18 983-984, October 2008; hereby incorporated by reference in its entirety.

MiR may be amplified by any of a number of techniques including reverse transcription followed by PCR. Some techniques of reverse transcription of miR use a targeted stem-loop primer to prime reverse transcription of the miR into a cDNA template. The cDNA template may then be used as a primer for any type of PCR including any type of quantitative PCR. A stem-loop oligonucleotide is a single stranded oligonucleotide that includes a sequence capable of binding to a specific marker because it includes a nucleic acid sequence complementary to the marker. The sequence complementary to the marker is flanked by inverted repeats that form self-complementary sequences. Such nucleotides may contain a fluorophore quencher pair at the 5' and 3' ends of the oligonucleotide. (See Buzdin and Lukyanov in *Nucleic Acids Hybridization Modern Applications*, pp 85-96, Springer 2007, hereby incorporated by reference in its entirety.)

Elements and acts in the examples are intended to illustrate the invention for the sake of simplicity and have not necessarily been rendered according to any particular sequence or embodiment. The example is also intended to establish possession of the invention by the Inventors.

EXAMPLES

Example 1

Under an Institutional Review Board approved protocol, NSCLC patients with brain metastasis (BM+) were identified. To be included in this study, CT chest, 18F-FDG PET/CT, and brain MRI imaging studies must have been performed within 30 days of one another. NSCLC patients without brain metastasis (BM−) were matched to BM+ by age, gender, histology, and stage at presentation. Multiple parameters were evaluated including primary tumor lesion metabolic activity on PET/CT using Standardized Uptake Measurements (SUVmax of brain, muscle, spleen, and chest nodal disease) by board certified radiologists. Summarization of clinical characteristics and breakdown of lung tumor based on histology of adenocarcinoma (AD) and squamous cell carcinoma (SCC) is shown in Table 1. RNA was extracted from the 12 formalin-fixed; paraffin embedded small cell lung cancer tumor specimens by manually scraping (macrodissection) the tumor from the slides followed by de-paraffinization with xylene. Total RNA was extracted using Trizol based reagent.

For qRT-PCR the GenoExplorer miRNA first-strand cDNA Core Kit (GenoSensor Corporation, Tempe, Ariz.) was used to generate miRNA first-strand cDNA. MiRNA expression levels were measured using miRNA specific forward primers and a universal reverse primer (GenoSensor Corporation, Tempe, Ariz.) in a SYBR green assay. The PCR reactions were carried out on in triplicate in a 384-well plate format with 15 µl reaction volumes according to the manufacturers instructions. Melting curve analysis was used to assess the specificity of the amplified product. Quantification of miRNA was carried out by converting the Ct values to an arbitrary number and then by normalizing the arbitrary number to a reference gene 5S-rRNA.

MiRNA was also analyzed via array profiling and expression was normalized to that of the reference gene 5S-rRNA. A comprehensive analysis of the miRNA data was conducted to find miRNA best able to distinguish between samples from patients with brain metastasis and samples from patients without brain metastasis (BM+ and BM−) samples, with that distinction confirmed by brain imaging.

An algorithm developed to analyze gene expression data (see Kim et al, reference 12 below) based on a mathematical model of contextual genomic regulation to identify cellular contexts was used to identify one or more miRNAs with a cohesive expression pattern in a specified condition with statistical significance. Briefly, the algorithm utilizes two statistical parameters, conditioning ($\delta_k$) and crosstalk ($\eta_k$), as given in equations 1 and 2, in order to determine if an miRNA k displays a cohesive expression pattern specific to a cellular context regulated by Y=1, where Xk is state of driven miRNAs. Conditioning measures the lack of transcriptional coherence in the condition of interest and crosstalk measures the specificity of coherence.

$$\delta_k = 1 - P(X_k=1 | Y=1), \quad (1)$$

$$\eta_k = P(X_k=1 | Y \neq 1) \quad (2)$$

This is based on the property that a cell deviates from its regulatory mechanism under environmental changes or in this study, more specifically, the presence of tumor. A change in the cellular context can be used to condition a subset of samples. The cellular contexts of interest in this study included the presence or absence of brain metastasis. Thus the method looks for miRNA with conditional, coherent expression in the BM+ condition. If the expression of a miRNA shows a consistent pattern in one condition (BM+,) but loses such consistency in another condition (BM−), then these statistics are further tested for their statistical significance using hypergeometric probability. miRNAs with low values for conditioning and crosstalk that displayed statistical significance between the two conditions were identified as targets. Storey's false discovery rate (FDR) was used to correct the statistical significance of the conditions.

Differential expression analysis aims at finding genes or miRNA that are significantly expressed in one condition relative to another. The Significance Analysis of Microarrays (SAM) method that assigns a score to each gene on the basis of change in gene expression relative to the standard deviation of repeated measurements (See Tusher et al, reference 16 below). For genes with scores greater than an adjustable threshold, SAM uses permutations of the repeated measurements to estimate the percentage of genes identified by chance. Combinations of validated miRNA and imaging biomarkers are selected to find a subset of all the given parameters that can best classify the BM+ and BM− groups. Multiple techniques, alone or in combination were used to identify biomarkers and compare the results. Such techniques include but are not limited to rank correlation, in-silico conditioning, and t-test.

Twelve PET/CT and 19 CT Scan features were obtained. These features were matched with the miRNA to obtain highly correlated miRNA and imaging features. Significant correlations were calculated using Spearman's rank correlation method with the ρ-value indicating the correlation. In-silico conditioning is done as described above. Absolute value two-sample t-test with pooled variance estimate using rank features function in MATLAB was used to perform the t-test.

The in-silico conditioning algorithm is used to find set of signatures coherent in a condition. Each of the following conditions were investigated separately: conditioning on the BM+ group against the BM− group and vice versa and conditioning on the BM− group against the BM+ group and vice versa.

Because the algorithm uses quantized values, the miRNA expression values were binarized based on the presence or absence of signal. Binarization is based on the fact that the relative strength of miRNA expression may not be statistically significant for biomarker identification. Table 2 shows results for BM− vs. BM+. Six miRNAs down regulated in BM− and up regulated in BM+, show commonality between the features selected by rank correlation. BM+ vs BM− also gave the same 6 statistically significant miRNA.

The top 20 differentially expressed miRNA found using SAM are shown in Table 3. A minimum 2-fold change between expression in BM+ and BM− was required for inclusion on the list. Eighteen miRNA were selected for qRT-PCR profiling based on in silico conditioning and differential expression analysis. These miRNA were also normalized with 5S-rRNA as a reference gene. A miR-650-pre was also added.

In-silico conditioning was used to condition the BM+ and BM− class labels and the top 11 miRNA were found by SAM. In-silico conditioning was further evaluated with qRT-PCR and used along with PET/CT and CT imaging characteristics. The results using PET/CT and miRNA are presented in Table 4 and CT with miRNA is presented in Table 7.

To evaluate the class separability of the selected features, the groups were clustered based on these features. In hierarchical clustering the data is grouped in several steps via a series of partitions. Thus in such a clustering a user can decide the number of clusters to keep. Hierarchical Clustering was done using Hierarchical clustering explorer HCE 3.0 (See Seo et al, Reference 17 below. Pearson's correlation coefficient is used as the similarity measure and complete linkage is used to calculate intercluster distance to merge two clusters.

Figure 2:
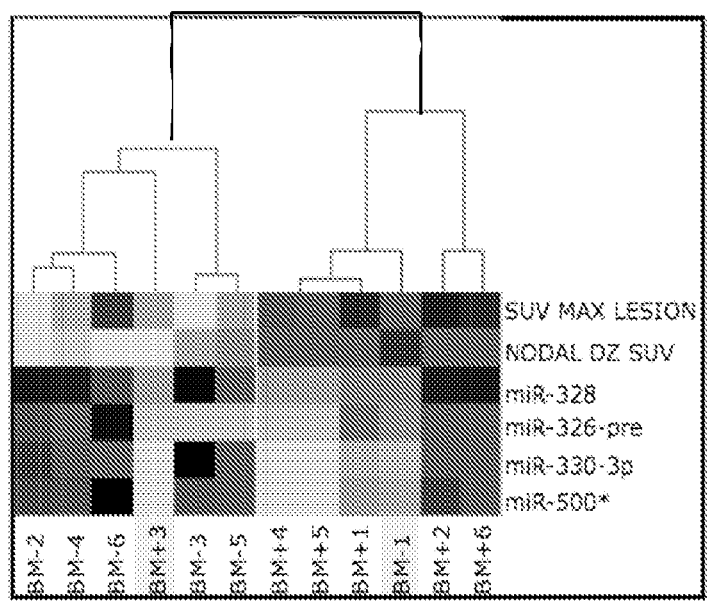
FIG. 2 depicts hierarchical clustering of samples with features selected via in-silico conditioning.
Figure 3:
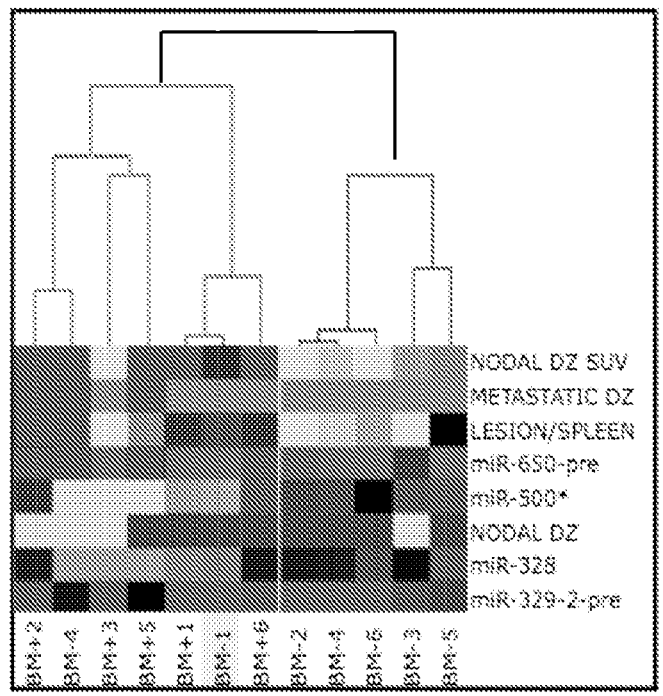
FIG. 3 depicts hierarchical clustering of samples with features selected via t-test.

Clustering results using Kendall's rank correlation is shown in FIG. 1, in-silico conditioning in FIG. 2 and t-test ranked features in FIG. 3. Rank correlation and in-silico conditioning based featured resulted in two incorrectly assigned samples, where as t-test features result in only one false positive.

Example 1 Tables:

TABLE 1

Clinical characteristics of patients and NSCLC.

|  | BM+ | BM− |
|---|---|---|
| No. Cases | 6 | 6 |
| Avg. volume (SD) | 72.52 (61.70) | 1660.84 (2771.64) |
| Gender | | |
| Male | 1/6 (16.6%) | 3/6 (50%) |
| Female | 5/6 (83.3%) | 3/6 (50%) |

TABLE 1-continued

Clinical characteristics of patients and NSCLC.

|  | BM+ | BM− |
|---|---|---|
| Cancer cell type | | |
| AD | 3/6 (50%) | 4/6 (66.6%) |
| SCC | 3/6 (50%) | 2/6 (33.3%) |

SD = Standard Deviation,
AD = Adenocarcinoma,
SCC = Squamous cell carcinoma.

TABLE 2 miRNA in BM− vs. BM+

| Name | CT | CD | p-value | BM−1 | BM−2 | BM−3 | BM−4 | BM−5 | BM−6 | BM+1 | BM+2 | BM+3 | BM+4 | BM+5 | BM+6 |
|---|---|---|---|---|---|---|---|---|---|---|---|---|---|---|---|
| label | 0.00 | 0.00 | 0.00 | 0 | 0 | 0 | 0 | 0 | 0 | 1 | 1 | 1 | 1 | 1 | 1 |
| hsa-miR-601 | 0.14 | 0.00 | 0.01 | 0 | 0 | 0 | 0 | 0 | 1 | 0 | 1 | 1 | 1 | 1 | 1 |
| hsa-miR-329-1-pre | 0.00 | 0.20 | 0.01 | 0 | 0 | 1 | 0 | 0 | 1 | 1 | 1 | 1 | 1 | 1 | 1 |
| hsa-miR-146b-pre | 0.29 | 0.00 | 0.03 | 0 | 0 | 0 | 0 | 0 | 0 | 0 | 1 | 1 | 1 | 1 | 1 |
| hsa-miR-500* | 0.14 | 0.20 | 0.05 | 1 | 0 | 1 | 1 | 1 | 1 | 0 | 0 | 0 | 0 | 0 | 0 |
| hsa-miR-092a | 0.14 | 0.20 | 0.05 | 1 | 0 | 1 | 1 | 1 | 1 | 0 | 0 | 0 | 0 | 0 | 0 |
| hsa-miR-495-pre | 0.14 | 0.20 | 0.05 | 0 | 0 | 1 | 0 | 0 | 0 | 1 | 1 | 1 | 1 | 1 | 1 |

CT = Crosstalk,
CD = Conditioning

TABLE 3

Differentially expressed miRNA in BM+ vs. BM−

| SAM | Fold Change | q-value |
|---|---|---|
| hsa-miR-329-1-pre | 133.02 | 0 |
| hsa-miR-326-pre | 94.24 | 0 |
| hsa-miR-495-pre | 123.44 | 0 |
| hsa-miR-500* | 106.19 | 0 |
| hsa-miR-326 | 84.30 | 0 |
| hsa-miR-370 | 57.51 | 0 |
| hsa-miR-601 | 38.29 | 0 |
| hsa-miR-325 | 61.25 | 0 |
| hsa-miR-330-3p | 53.02 | 0 |
| hsa-miR-218 | 51.50 | 0 |
| hsa-miR-143 | 37.75 | 0 |
| hsa-miR-146b-pre | 35.59 | 0 |
| hsa-miR-450-2-pre | 38.72 | 0 |
| hsa-miR-122a | 30.13 | 0 |
| hsa-miR-452-pre | 39.78 | 0 |
| hsa-miR-092-1-pre | 32.96 | 0 |
| hsa-miR-340-3p | 27.86 | 0 |
| hsa-miR-342-3p | 24.30 | 0 |
| hsa-miR-328 | 64.19 | 0 |
| hsa-miR-1233 | 26.91 | 0 |

TABLE 4

Correlaton between miRNA and Clinical Characteristics from PET/CT

| miRNA | Imaging Characteristics | ρ | p-value |
|---|---|---|---|
| miR-328 | SUV MAX LESION | −0.657 | 0.028 |
|  | SUV MAX SPLEEN | −0.722 | 0.012 |
| ma-346 | Gender | 0.620 | 0.042 |
|  | SUV MAX BRAIN | 0.510 | 0.026 |
| miR-329-2-pre | Gender | −0.659 | 0.027 |
|  | SUV MAX MUSCLE | −0.616 | 0.044 |
|  | SUV MAX BRAIN | −0.644 | 0.033 |
|  | SUV NODAL DISEASE | −0.641 | 0.034 |
| miR-650-pre | SUV MAX MUSCLE | −0.713 | 0.014 |

TABLE 4-continued

Correlaton between miRNA and Clinical Characteristics from PET/CT

| miRNA | Imaging Characteristics | ρ | p-value |
|---|---|---|---|
| miR-326-pre | SUV MAX LESION | −0.639 | 0.034 |
|  | SUV MAX SPLEEN | −0.752 | 0.008 |
| miR-330-3p | SUV MAX SPLEEN | −0.785 | 0.004 |
| miR-500* | SUV MAX SPLEEN | −0.621 | 0.042 |

TABLE 5 miRNA and PET/CT features selected by in silico conditioning

| Name | CT | CD | p-value | BM−1 | BM−2 | BM−3 | BM−4 | BM−5 | BM−6 | BM+1 | BM+2 | BM+3 | BM+4 | BM+5 | BM+6 |
|---|---|---|---|---|---|---|---|---|---|---|---|---|---|---|---|
| SUV MAX LESION | 0.17 | 0.17 | 0.04 | 1 | 0 | 0 | 0 | 0 | 0 | 1 | 1 | 0 | 1 | 1 | 1 |
| NODAL DZ SUV | 0.17 | 0.17 | 0.04 | 1 | 0 | 0 | 0 | 0 | 0 | 1 | 1 | 0 | 1 | 1 | 1 |
| miR-328 | 0.50 | 0.00 | 0.09 | 1 | 1 | 1 | 1 | 1 | 1 | 1 | 1 | 0 | 0 | 1 | 0 |
| miR-326-pre | 0.50 | 0.00 | 0.09 | 1 | 1 | 1 | 1 | 1 | 1 | 1 | 1 | 0 | 0 | 1 | 0 |
| miR-330-3p | 0.50 | 0.00 | 0.09 | 1 | 1 | 1 | 1 | 1 | 1 | 1 | 1 | 0 | 0 | 1 | 0 |
| miR-500 | 0.50 | 0.00 | 0.09 | 1 | 1 | 1 | 1 | 1 | 1 | 1 | 1 | 0 | 0 | 1 | 0 |

TABLE 6 miRNA and CT Features selected by In-Silico Conditioning

| Features | CT | CD | p-value | BM−1 | BM−2 | BM−3 | BM−4 | BM−5 | BM−6 | BM+1 | BM+2 | BM+3 | BM+4 | BM+5 | BM+6 |
|---|---|---|---|---|---|---|---|---|---|---|---|---|---|---|---|
| DIST | 0.33 | 0.00 | 0.03 | 1 | 1 | 1 | 1 | 1 | 1 | 0 | 0 | 1 | 0 | 0 | 1 |
| miR-328 | 0.050 | 0.00 | 0.09 | 1 | 1 | 1 | 1 | 1 | 1 | 1 | 1 | 0 | 0 | 1 | 0 |
| miR-326-pre | 0.50 | 0.00 | 0.09 | 1 | 1 | 1 | 1 | 1 | 1 | 1 | 1 | 0 | 0 | 1 | 0 |
| miR-330-3p | 0.50 | 0.00 | 0.09 | 1 | 1 | 1 | 1 | 1 | 1 | 1 | 1 | 0 | 0 | 1 | 0 |
| miR-500* | 0.50 | 0.00 | 0.09 | 1 | 1 | 1 | 1 | 1 | 1 | 1 | 1 | 0 | 0 | 1 | 0 |
| SHAPE | 0.17 | 0.33 | 0.12 | 0 | 1 | 1 | 0 | 0 | 0 | 1 | 1 | 1 | 0 | 1 | 1 |
| PO | 0.33 | 0.17 | 0.12 | 1 | 1 | 1 | 1 | 1 | 0 | 0 | 0 | 1 | 0 | 0 | 1 |
| MARGIN | 0.50 | 0.17 | 0.27 | 1 | 0 | 1 | 1 | 1 | 1 | 0 | 1 | 0 | 0 | 1 | 1 |
| miR-370 | 0.50 | 0.17 | 0.27 | 1 | 1 | 1 | 0 | 1 | 1 | 1 | 0 | 0 | 1 | 0 | 0 |
| M. E. MAX | 0.33 | 0.33 | 0.28 | 0 | 1 | 0 | 0 | 0 | 1 | 1 | 1 | 1 | 0 | 0 |  |
| P. EFFUSIONS | 0.33 | 0.33 | 0.28 | 0 | 0 | 1 | 1 | 1 | 1 | 1 | 0 | 0 | 0 | 0 | 1 |

DIST = Distribution,
PO = Post Obstruction,
ME Max = Max Muscle Enhance,
P = Pleural

TABLE 7

Correlation between miRNA and Clinical Characteristics from CT.

| miRNA | Imaging Characteristics | ρ | p-value |
|---|---|---|---|
| miR-346 | 3$^{RD}$ DIMENSION | −0.648 | 0.023 |
|  | VOLUME | −0.591 | 0.043 |
| miR-193-pre | CAVITATION | −0.784 | 0.003 |
| miR-326 | NODAL | 0.591 | 0.043 |
| miR-370 | METS | −0.659 | 0.020 |

ENH = Enhancement

Example 2

Brain metastasis (BM) can affect up to 25% of non-small cell lung cancer (NSCLC) patients during their lifetime. Efforts to characterize patients that will develop BM have been disappointing.

miRNA microarray profiling was performed on samples from clinically matched lung NSCLC from patients with BM (BM+) and without BM (BM−). A T-test was used to select the top 19 miRNA candidates for validation by qRT-PCR. qRT-PCR confirmed miRNAs were then subjected to a multivariate analysis to identify the fewest miRNA needed to differentiate between BM+ and BM−, and validated on an independent validation cohort.

Of the 19 miRNA candidates identified by microarray analysis, 8 were confirmed to be significantly differentially expressed by qRT-PCR. Of these 8 miRNA targets, the expression of hsa-miR-328 and hsa-miR-330-3p were able to correctly classify BM+ vs BM− patients. The classifier was used in two validation sets and correctly classified 12/15 patients. We next showed that NSCLC cells stably transfected with hsa-miR-328 had higher migratory potential than the parental NSCLC cells. Next, we conducted gene expression analysis comparing NSCLC parental and stably transfected miR-328 cells and identified several significantly differentially expressed genes, whose expression might be directly or indirectly regulated by miR-328.

miRNA profiling for lung cancer has been previously conducted by various groups to predict patient survival (See Reference 9). These profiles have also been correlated with clinicopathological parameters of lung cancer patients (See References 9-11). Recently, Bishop et al, used this approach for classification of NSCLC (See Reference 12). Several miRNAs have been associated with the key regulatory pathways such as EGFR (See Reference 13) and KRAS (See Reference 14).

This study was conducted under an Institutional Review Board (IRB) approved protocol. BM+ and BM− NSCLC patients identified through the Scottsdale Healthcare (SHC) tumor registry diagnosed during the periods Jan. 1, 2003 to Dec. 30, 2006 with formalin-fixed, paraffin-embedded (FFPE) tumor tissue available were included in a previously published study (See Reference 15). To be included in this miRNA discovery study, the pre-requisites were performance of a computed tomography (CT) of the chest, whole-body 2-[$^{18}$F]-Fluoro-2-Deoxy-D-Glucose positron emission computed tomography-CT (FDG-PET CT), and brain magnetic resonance imaging (MRI) imaging study within 30 days of one another for each patient. Where possible, BM− NSCLC patients were matched to BM+ NSCLC patients by age, gender, histology, and stage at presentation. For this discovery cohort, 7 patients with BM+ and 6 patients with BM− NSCLC were included (Table 8).

For validation of our miRNA profiling results, an independent cohort of 15 NSCLC patients with FFPE lung tumor tissue who underwent surgical resection at SHC between March 2001 and November 2006 were included under IRB approval (SHC Validation). These patients underwent preoperative evaluation per common practice guidelines including CT chest, FDG-PET CT, and either CT or MRI of the brain (Table 8).

Twenty-four NSCLC cases from the University of Iowa Hospitals and Clinics (IOWA) collected under an IRB approved protocol were also included, as an independent dataset for testing. These samples were all collected from metastatic brain lesions and flash frozen and stored in liquid nitrogen until the time of RNA extraction.

RNA Extraction and miRNA Microarray Profiling

RNA was extracted from all FFPE NSCLC tumor specimens by manually scraping (macrodissection) the tumor tissue from the slides followed by de-paraffinization with xylene. Total RNA was extracted following standard protocols using phenol and guanidine thiocyanate. The concentration and purity of isolated RNA was estimated using the ND-1000 micro-spectrophotometer (NanoDrop Technologies, Wilmington, Del.). A minimum of 1 µg of total RNA was added to GenoExplorer™ microRNA Expression System (GenoSensor Corporation, Tempe, Ariz.) containing probes in triplicate for 678 validated human mature miRNAs with an additional 473 validated human pre-miRNAs (Sanger miRNA Registry, version 12.0 September 2008 http://www.mirbase.org) along with positive and negative control probes (See Reference 16). One miRNA microarray chip hybridization was performed per patient sample.

Identification of Candidate miRNA Biomarkers miRNA expression was estimated from microarray profiling and was normalized with the reference gene 5S-rRNA after a thorough evaluation of several normalization techniques such as using a simple global scaling factor as in MAS 5.0 approach (See Reference 17) scale and median-shift method as used in (See References 18 and 19) normalization with non-variant miRNA from the dataset (See Reference 20) and normalization with house-keeping genes (See Reference 21).

Differential expression analysis aims at finding genes or miRNAs that are significantly expressed in one condition in contrast to the other. We used a two-sided t-test to identify differentially expressed miRNAs between the BM+ and BM− samples. The p-values generated from the t-test were corrected for multiple hypotheses testing using Benjamini-Hochberg correction (See Reference 22).

Correlation coefficients between BM+ and the clinical parameters: age, gender and histology were computed using Spearman's rank correlation. Similarly, correlation coefficients were also computed for miRNA with age, gender, and histology.

Quantitative Reverse Transcription PCR (qRT-PCR) Analysis of miRNAs

Confirmation of the top 19 differentially expressed miRNAs in BM+ versus BM− was performed using qRT-PCR by using the total RNA extracted from these samples. The GenoExplorer™ miRNAFirst-strand cDNA Core Kit (#2002-50, GenoSensor Corporation, Tempe, Ariz.) was used to generate miRNA first-strand cDNA. MiRNA expression levels were measured using miRNA specific forward primers and a universal reverse primer (GenoSensor Corporation, Tempe, Ariz.) in a SYBR green assay (#04887352001, Roche, Indianapolis, Ind.) (See Reference 16).

The PCR reactions were carried out in triplicate in a 384-well plate format with 15 µl reaction volume using Lightcycler 480 (Roche, Indianapolis, Ind.). The PCR reaction conditions were 15 minutes denaturation at 94° C. followed by 45 cycles of 94° C. for 30 seconds, 59° C. for 15 seconds and 72° C. for 30 seconds. Melting curve analysis was used to assess the specificity of the amplified product. Quantification of these miRNAs was carried out using delta-delta CT normalizing the result to the reference gene 5S-rRNA (See Reference 23).

Class Prediction Via Strong-Feature Set Algorithm

Strong-feature set algorithm: To identify the best and minimal features for predicting BM of NSCLC patients, based on the expression of miRNAs, we used the "strong features method" developed previously, as a classifier model (See Reference 24). The model is a simple linear classifier with noise injection but modified to speed up the computation through analytical solution, instead of a Monte-Carlo simulation. The method has been developed to mitigate overfitting problem in classifier design with small number of samples, by designing a classifier from a probability distribution resulting from spreading the mass of the sample points to make classification more difficult, while maintaining sample geometry.

Feature selection: As we focus on only eight miRNAs (hsa-miR-325, hsa-miR-326, hsa-miR-328, hsa-miR-329-2-pre, hsa-miR-330-3p, hsa-miR-500*, hsa-miR-370 and hsa-miR-650-pre), taken forward from the differential expression analysis to measure by PCR, we performed full combinatorial search to identify best strong-features set. PCR measurements made from the same patient samples we used for screening of miRNA profiling data (BM data) were used for feature selection. For each combination of features (among $255=2^8-1$), we used the leave-one-out method to estimate classification error. Feature set with the lowest leave-one-out error was deemed the best strong-feature set.

Classifier design for prediction: Once the best strong-feature set is identified as described above, all the samples in discovery cohort were used to design a classifier to predict BM of patients. In all classifier designs, the amount spread was set to 0.4, according to the suggestion made by Kim et al (See Reference 24).

Validation on independent data set: The normalized PCR measurements were further processed by dividing the difference between its value and its mean across all the samples, i.e. z-score. Hence, each miRNA has zero mean and the standard deviation of one. This was done for both discovery and validation data set, separately.

Construction of Stable Lentiviral Clones

A549 NSCLC cell line was obtained from ATCC (Manassas, Va.) and maintained in RPMI-1640 medium supplemented with 10% FCS. Lentiviral constructs expressing GFP-empty vector or GFP vector over-expressing miR-328 were obtained from Systems Biosciences Inc. (Mountain View, Calif.). Virus production and cell transduction in A549 cells was performed as described (See Reference 25) and GFP positive cells were flow sorted.

Migration Assay

To determine the effect of miR-328 over-expression in migration of A549 cells, we used a modified microwell Boyden chamber assay as described previously (See Reference 26). Briefly, RPMI 1640 medium supplemented with 10% FCS was added to the lower wells of a 12 well modified Boyden chamber (Neuroprobe, Cabin John, Md.). Wells were covered with an 8-μm pore size Nucleopore filter (Neuroprobe) that had previously been coated with 50 μg/mL Purecol® (Bovine collagen) (Advanced Biomatrix, San Diego, Calif.). A549 GFP-empty vector control cells and A549 miR-328 over-expressing cells were suspended at the concentration of $4.8 \times 10^4$ cells in 100 μl of assay medium (RPMI 1640 medium supplemented with 10% FCS) and seeded into the upper wells. After incubation for 5 hours at 37° C., non-migrated cells were scraped off from the upper side of the filter, and filters were stained with 4',6-diamidino-2-phenylindole (DAPI). Nuclei of migrated cells were counted in 5 high-power fields (HPF) with a 20× objective. Values were assessed in triplicate.

mRNA Expression Profiling

For each experimental sample, $3 \times 10^5$ cells were seeded in duplicate using standard growth conditions. After 24 hours, total RNA was isolated according to manufacturer's protocol (mirVana miRNA Isolation Kit, Ambion, Austin, Tex.). Total RNA yield was assessed using a NanoDrop 2000c (Thermo Scientific, Wilmington, Del.), and quality was assessed on a BioAnalyzer 2400 using a BioAnalyzer RNA 6000 Nano LabChip Kit (Agilent Technologies, Palo Alto, Calif.). RNA from A549 GFP-empty vector and A549-GFP-over-expressing miR-328 were analyzed for mRNA expression profiling. A quick-amplification kit (Agilent, Santa Clara, Calif.) was used to amplify and label 500 ng target mRNA species to complementary RNA (cRNA) for oligo microarrays according to the manufacturer's protocol. For each array, experimental samples were run in duplicate along with a commercial universal reference RNA (Stratagene, La Jolla, Calif.) were labeled with cyanine 5-CTP and cyanine-3-CTP (Perkin Elmer, Boston, Mass.), respectively. cRNA concentration and labeling efficiency was measured spectrophotometrically. Approximately 800 ng of both Cy5-labeled experimental cRNA and Cy3-labeled universal reference RNA were hybridized to each microarray (adjusting for labeling efficiency).Whole human genome 4×44K microarrays were hybridized and washed following Agilent's protocol. Images were captured using an Agilent DNA microarray scanner set at default settings for gene expression. Scanned images were processed using Feature Extractor v. 10.5.1.1. By applying a LOWESS (locally weighted linear regression) correction for dye-bias, background noise was subtracted from spot intensities. To filter the preprocessed data, genes with a background signal higher than feature signal were removed.

Differentially Expressed Genes

To identify the genes regulated by miR-328 we performed differential analysis on the two samples within A549 control cells and A549-miR-328 over-expressed cells. Differentially expression analysis aimed at finding genes that were up-regulated or down regulated for miR-328 over expression and was done using two sided t-test. p-values generated from t-test were corrected for multiple hypotheses testing using Benjamini-Hochberg correction.

Patient Samples

FFPE tumor specimens (n=13) were obtained and total RNA was extracted. The 13 FFPE tumor samples yielded approximately 0.5 to 5 μg of total RNA. Twelve of them (six BM+ and six BM−) had sufficient total RNA yield to perform miRNA microarray profiling. All seven BM− samples (including BM-2 which was not miRNA profiled) were evaluated by qRT-PCR. One BM+ sample that was miRNA microarray profiled had insufficient additional RNA for qRT-PCR analysis (sample BM+7). Fifteen samples were included in the SHC validation set. All the samples had good RNA yields varying between 1.4 μg to 10 μg. Twenty-four IOWA cases were available as an independent data set for validation, and all samples successfully had RNA extracted for qRT-PCR analysis. The 24 IOWA samples yielded approximately 0.05 to 1 μg of total RNA. The clinical characteristics of the SHC Discovery patients (n=13), SHC Validation (n=15), and IOWA cases (n=24) are listed in Table 8.

TABLE 8

Clinical Characteristics of Patients and NSCLC tumors

| | Discovery SHC Cohort | | IOWA NSCLC Brain Metastasis Tumor | Validation SHC |
|---|---|---|---|---|
| | BM+ | BM− | Tissue | Cohort |
| No. of cases | 7 | 6 | 24 | 15 |
| Median Age years (range) | 58 (53-74) | 66.5 (60-71) | 60.5 (38-77) | 65 (46-78) |
| Gender | | | | |
| Male | 1/7 (14.3%) | 3/6 (50%) | 13/24 (54.2%) | 5/15 (33.3%) |
| Female | 6/7 (85.7%) | 3/6 (50%) | 11/24 (45.8%) | 10/15 (66.7%) |
| Histology | | | | |
| Adenocarcinoma | 4/7 (57.1%) | 4/6 (66.6%) | 14/24 (58.4%) | 9/15 (60%) |
| Squamous cell carcinoma | 3/7 (42.9%) | 2/6 (33.3%) | 5/24 (20.8%) | 3/15 (20%) |
| NSCLC NOS[#]/Other | — | — | 5/24 (20.8%) | 3/15 (20%) |

TABLE 9

Differentially Expressed miRNAs in BM+ vs. BM− NSCLC (adapted from Reference 40)

| miRNA | Fold Change | p-value(Corrected) |
|---|---|---|
| hsa-miR-329-1-pre | 133.02 | 0.02174 |
| hsa-miR-326-pre | 94.24 | 0.02174 |
| hsa-miR-495-pre | 123.45 | 0.02174 |
| hsa-miR-500* | 106.19 | 0.02574 |
| hsa-miR-326 | 84.30 | 0.03198 |
| hsa-miR-370 | 57.52 | 0.03198 |
| hsa-miR-218 | 51.50 | 0.03198 |
| hsa-miR-330-3p | 53.02 | 0.03198 |
| hsa-miR-122a | 30.13 | 0.03198 |
| hsa-miR-325 | 61.25 | 0.03198 |
| hsa-miR-489-pre | 34.39 | 0.03658 |

TABLE 9-continued

Differentially Expressed miRNAs in BM+ vs. BM− NSCLC (adapted from Reference 40)

| miRNA | Fold Change | p-value(Corrected) |
|---|---|---|
| hsa-miR-599 | 40.42 | 0.03658 |
| hsa-miR-328 | 64.19 | 0.03669 |
| hsa-miR-329-2-pre | 39.19 | 0.03669 |
| hsa-miR-346 | 25.31 | 0.03673 |
| hsa-miR-650-Pre | 13.58 | 0.03874 |
| hsa-miR-92a | −3.41 | 0.04126 |
| hsa-miR-193-pre | 16.12 | 0.04126 |
| hsa-miR-103 | 10.21 | 0.04901 |

This table shows the top best differentially expressed miRNA found by t-test. The p-values are corrected using Benjamini-Hochberg method (See Reference 22) Fold change here represents the fold change in BM+ versus BM−.

SHC Discovery Set

The data obtained by miRNA profiling of RNA isolated from the SHC Discovery samples was first analyzed using t-test analysis. Table 9 shows the top 19 significantly differentially expressed miRNAs in BM+ versus BM− NSCLC samples. The fold change for the top 19 miRNA array expression for BM+ compared with BM− ranged from down-regulation in BM+ by 3.41 fold for miR-92a to up-regulation of 133 fold for miR-329-1-pre, respectively. These miRNAs were subjected to qRT-PCR analysis for confirmation. To confirm the results of miRNA profiling, qRT-PCR was performed using specific miRNA primers on the cDNA prepared from RNA isolated from FFPE samples. Of the top 19 miRNA candidates pulled by t-test analysis on miRNA profiling results, 8 miRNAs were confirmed by qRT-PCR to be significantly differentially expressed. The following miRNAs were high in BM+ samples compared to BM− samples when measured by both miRNA profiling and qRT-PCR analysis miR-326, -370, -330-3p, -500*, -328, -325, -329-2-pre, and -650-pre. Correlation coefficients between BM+ and clinical parameters age, gender and histology did not show significant correlations. Similarly, correlation coefficients were also computed for the most discerning miRNAs. There were no significant correlations between these eight miRNAs with age, gender, or histology.

Design and Validation of miRNA Classifier for BM

Strong Feature Results

Figure 4:
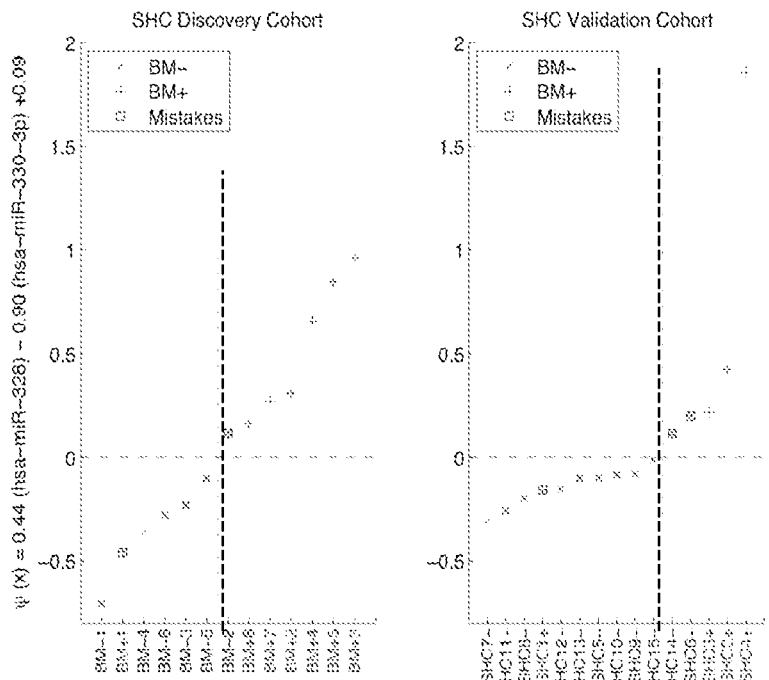
FIG. 4 depicts the ability of the test to differentiate lung tissue from BM− and BM+ patients in both the discovery and validation cohort using miR-328 and miR-330-3p.
Figure 5:
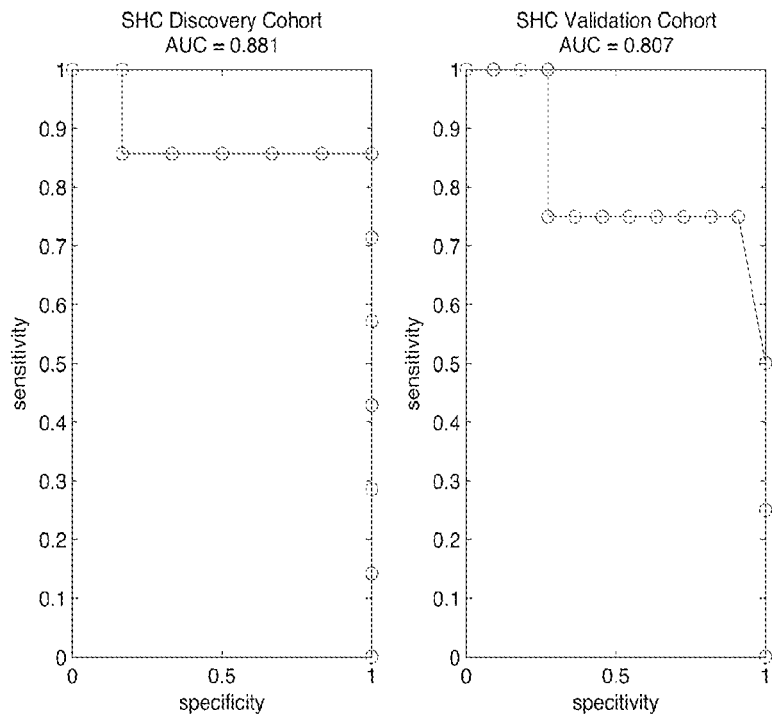
FIG. 5 depicts the Area Under the Curve (AUC) for the discovery and validation cohorts.

Upon testing of all possible combinations of feature set, the combination of miR-328 and miR-330-3p was deemed the best markers with the leave-one-out error of 3 out of 13 (0.2308), using SHC discovery data. We then designed a classifier with these two miRNAs from the same data set. FIG. 1A shows the prediction of the classifier on the same data set, misclassifying BM+1 and BM−2, resulting in 84.6% accuracy (re-substitution error) which corresponds to sensitivity=0.8571 and specificity=0.8333. We then applied the same classifier to the SHC validation data and the result is shown in FIG. 1B. Three samples were misclassified, SHC1+, SHC6− and SHC14−, with 80% accuracy (sensitivity=0.7500 and specificity=0.8182). To evaluate the robustness of the classifier, we performed ROC analysis and the results are shown in FIG. 4. AUC were 0.881 and 0.807 for SHC discovery data and SHC validation data sets, respectively. The expression of miR-328 in BM+ vs. BM− in the SHC validation cohort is shown in FIG. 5, it clearly shows that miR-328 is over-expressed in BM+ cases as compared to BM− cases (p=0.02). In addition, BM samples from the IOWA validation set also showed miR-328 over-expression as compared to BM− cases from SHC validation cohort (FIG. 5).

Role of miR-328
Cell Migration

Figure 6:
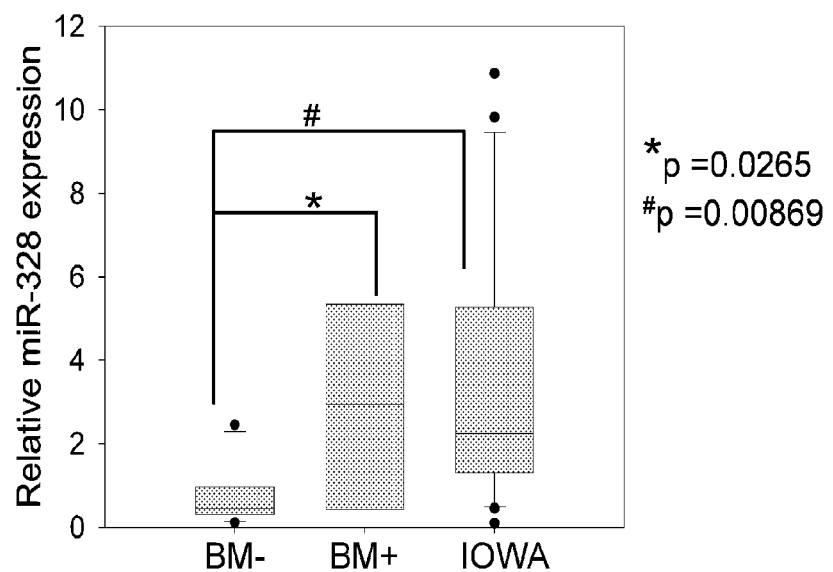
FIG. 6 depicts a box plot showing the relative expression of miR-328 in the validation cohort and in a set of samples from brain metastases (IOWA) Expression was normalized to the expression of 5S and RNU6 expression in all samples. miR-328 expression in A549 cells was used as a reference.
Figure 7:
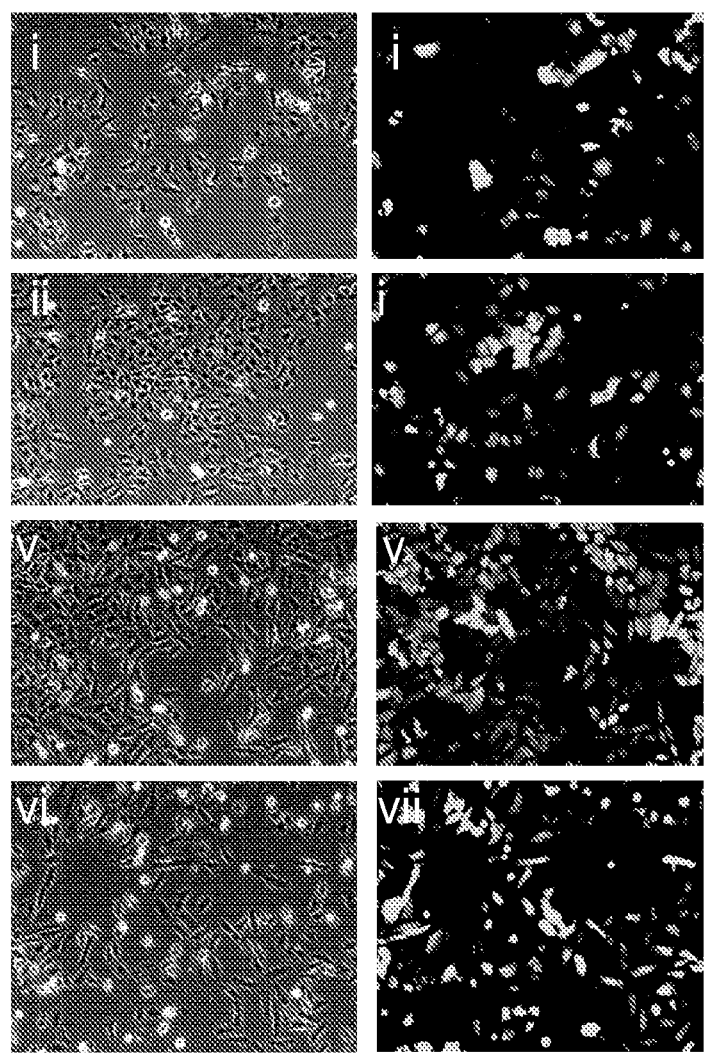
FIG. 7 depicts a panel of images from A549 and H1703 cells (i and iii), phase contrast images of A549-GFP and miR-238-GFP positive cells (ii and iv), corresponding GFP positive images (v and vii) and phase contrast images of H1703-GFP and miR-328-GFP cells (vi and viii). Magnification×10.
Figure 8:
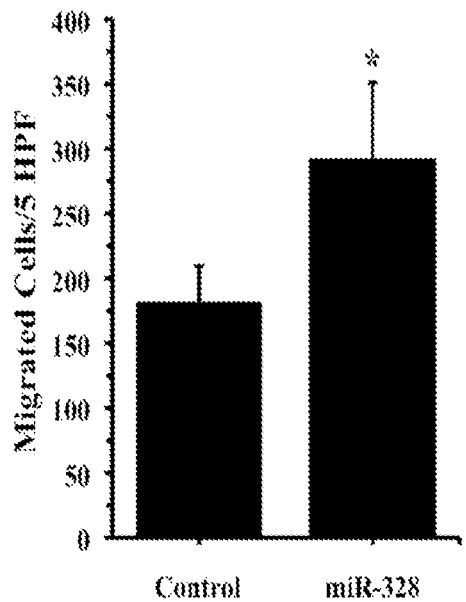
FIG. 8 depicts a graph showing migration of GFP-empty vector cells and GFP-miR-328 overexpressing cells in cell line A549.

We constructed stable lentiviral construct expressing GFP-empty vector and GFP with miR-328 over-expression in A549 lung adenocarcinoma cells (A549-empty and A549-328; respectively)(FIG. 6). Next, we used these cells in a modified Boyden chamber assay and counted the number of migratory cells. The results showed that ~1.7 fold more cells (A549-328) had migrated as compared to the A549-empty cells (p=0.016) (FIGS. 7, 8). These results suggest that miR-328 confers migratory potential to cancer cells and might be responsible for BM in NSCLC patients.

Gene Expression Analysis

Figure 12:
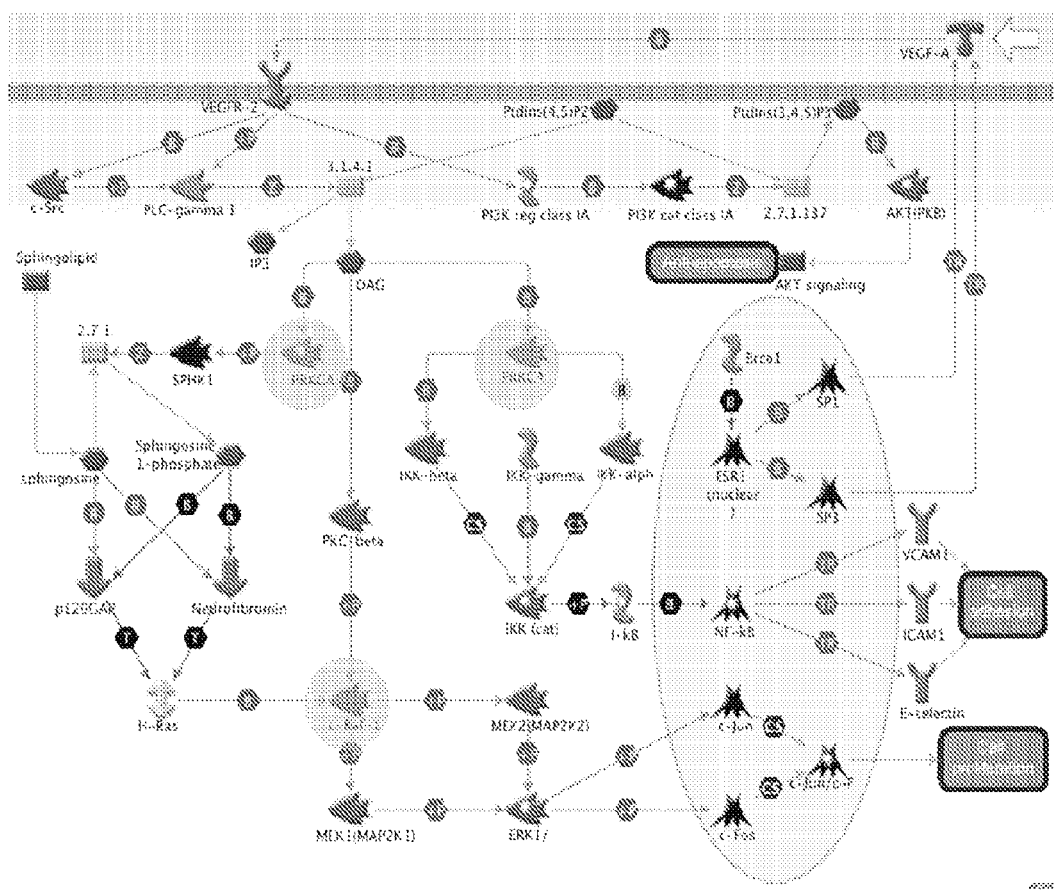
FIG. 12 depicts one example of a pathway (VEGF signaling) that might be affected as a result of a deregulated miR-328. Rafl and PRKCA were both upregulated in A549-miR-328 overexpressing cells.

In order to identify the direct and indirect targets of miR-328, we used the A549-328 and A549-empty cells for gene expression analysis. The hybridizations were performed in duplicate. We generated a list of 363 genes whose expression was up- or down-regulated at least 2 fold when the two conditions were compared. Next, we performed a search for potential targets for miR-328 using TargetScan's conserved seed pairing algorithm to find targets within conserved sites. (See Reference 27) The method predicted 108 conserved sites and 2573 poorly conserved sites. An overlap of all the predicted targets and the 363 potential targets found by differential expression analysis on the A549 cell lines gave us 27 targets (FIG. 4A-B). These targets were then plugged into a pathway analysis tool (GeneGo) to identify pathways that might be affected by these potential targets of miR-328. An example of a pathway that might be affected by miR-328 is shown in FIG. 12. This is the VEGF signalling pathway and we see that at least 2 of the miR-328 target genes play a key role in controlling this signaling pathway which leads to increased cell adhesion and motility.

Figure 9:
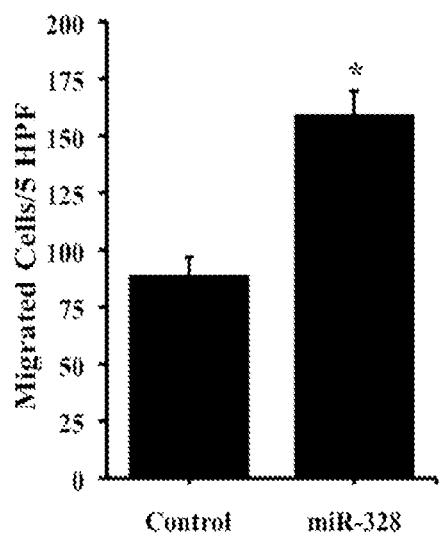
FIG. 9 depicts a graph showing migration of GFP-empty vector cells and GFP-miR-328 overexpressing cells in cell line H1703.
Figure 10:
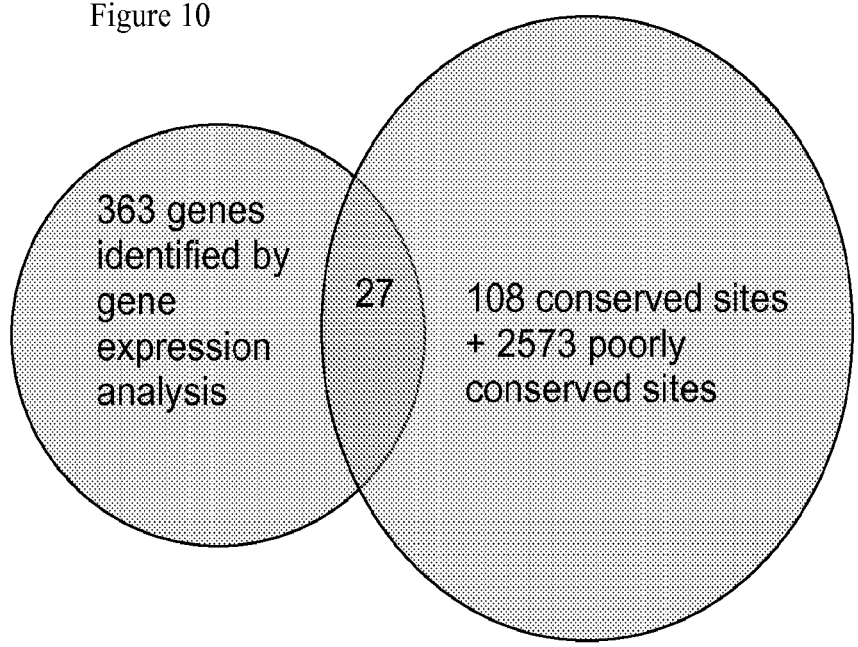
FIG. 10 depicts a Venn Diagram showing the overlap of 27 genes common between gene expression results and predicted miR-328 targets.
Figure 11:
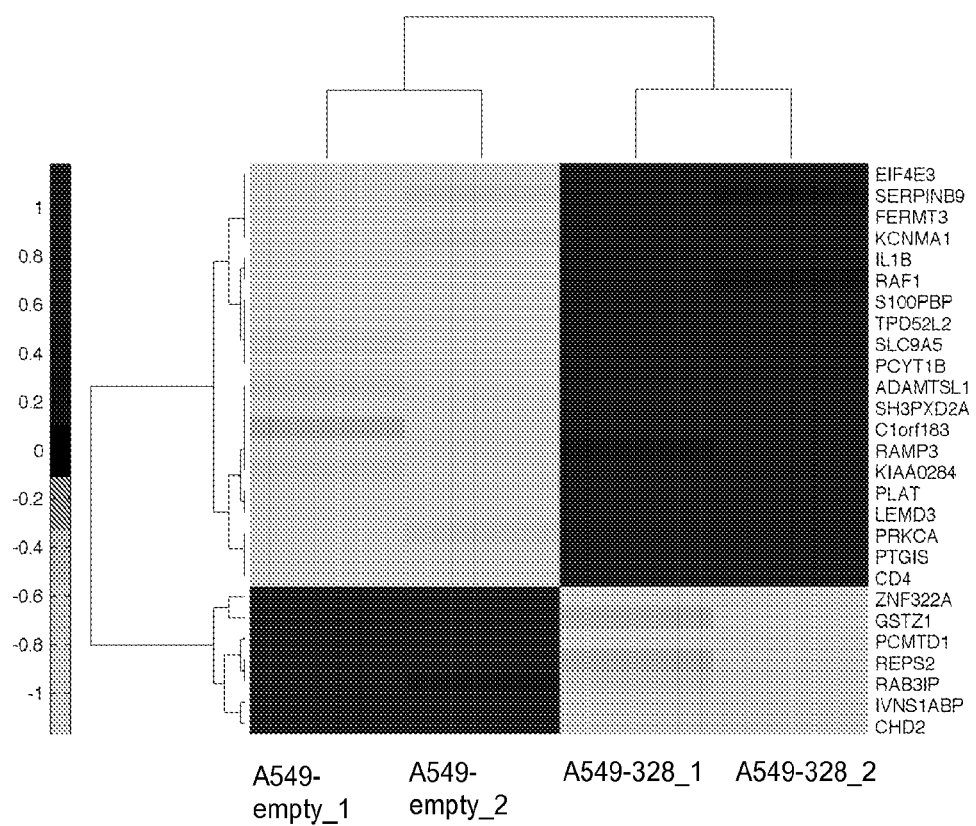
FIG. 11 depicts a Heat Map showing clustering of A549-mir-328 overexpressing cells and A549-empty cells using 27 genes.

Referring now to FIGS. 8 and 9, Both the A549 and H1703 cell lines demonstrated a significant increase in cell migration relative to the empty vector control when miR-328 is overexpressed. [p=0.016 (A549) and 0.0015 (H1703)]. Plotted values are mean+standard deviation of triplicate determinations. HPF: High Power Fields.

REFERENCES

So as to reduce the complexity and length of the Detailed Specification, Inventors herein expressly incorporate by reference all of the following materials to the greatest extent allowed.

1. Jemal A, et al, *CA Cancer J Clin*, 59, 225-249 (2009).
2. Grinberg-Rashi H et al, *Clin Cancer Res* 15, 1755-1761 (2009).
3. Laack NN and Brown P D. Semin Oncol 31, 702-713 (2004).
4. Oh Y et al, *Cancer* 115, 2930-2938 (2009).
5. Pugh T J and Gaspar L E, *Clin Lung Cancer* 8, 365-368 (2007).
6. Gore E M et al, *J Clin Oncol* (Meeting Abstracts) 27, 7506 (2009).
7. Lu J et al, *Nature* 435, 834-838 (2005).
8. Liu C G et al, *Nat Protoc* 3, 563-578 (2008).
9. Landi M T et al, Clin Cancer Res 16: 430-41 (2010)
10. Gallardo E, Carcinogenesis 30, 1903-1909 (2009).
11. Gao W et al, *Biomed Pharmacother* EPub Ahead of Print 25 Feb. 2010.
12. Bishop J A et al, Clin Cancer Res 16 610-619 (2010).
13. Seike M, *Proc Natl Acad Sci USA* 106 12085-12090 (2009).
14. Chin L J et al, *Cancer Res* 68, 8535-8540 (2008).
15. Nasser S *Proceeding of the IEEE International Conference on Bioinformatics & Biomedicine*, in press.
16. Ranade A R, *Journal of Thoracic Oncology* in press.

17. Affymetrix. Microarray Suite 5.0 User's Guide. Affymetrix edition. (2002).
18. Gene Spring: http://www.chem.agilent.com/Library/usermanuals/Public/GeneSpring GX10_QuickStartGuide.pdf.
19. Sanzari J K et al, *Radiat Res* 172, 437-443 (2009).
20. Andersen C L et al, Cancer Res 64, 5245-5250 (2004).
21. Perkins D O et al, Genome Biol 8, R27 (2007).
22. Benjamini Y et al, *Behav Brain Res,* 125, 279-284 (2001).
23. Livak K J and Schmittgen T D, Methods 25, 402-408 (2001).
24. Kim S, et al, J Comput Biol 9, 127-146 (2002).
25. Coleman J E et al, *Physiol Genomics* 12, 221-228 (2003).
26. Lamszus K et al, *Int J Cancer* 75, 19-28 (1998).
27. Lewis B P et al, Cell 120, 15-20 (2005).
28. Kumar M S et al, *Proc Natl Acad Sci USA* 105, 3903-3098 (2008).
29. Yu S L et al, *Cancer Cell* 13, 48-57 (2008).
30. Liu X et al, *J Clin Invest* 120, 1298-1309 (2010).
31. Hu Z et al, *J Clin Oncol* 28, 1721-1726 (2010).
32. Zhang J G et al, *Clin Chim Acta* 411, 846-852 (2010)
33. Graesslin O et al, *J Clin Oncol* 28, 2032-2037 (2010).
34. Eiring A M et al, *Cell* 140, 652-665 (2010).
35. Pan Y Z et al, *Mol Pharmacol* 75, 1374-1379 (2009).
36. Wang C H et al, *PLoS One* 3, e2420 (2008).
37. Boissonneault V et al, *J Biol Chem* 284, 1971-1981 (2009).
38. Bos P D et al, *Nature* 459 1005-1009 (2009).
39. Khaitan D et al, *BMC Cancer* 9, 258 (2009).
40. Nasser S et al, BIBM 2009 Proceeding of the IEEE International Conference on Bioinformatics & Biomedicine (in press).
41. "Cancer facts and figures 2009," American Cancer Society, Atlanta, Ga., Tech. Rep.,
42. Eisner R M et al, "Cancer statistics review, 1975-2002," National Cancer Institute, Bethesda, Md., Tech. Rep., April 2009.
43. Rutman A M and Kuo M D, *Eur J Radiol,* 70,232-241 (2009).
44. Lee R C et al, *Cell* 75,843-854 (1993)
45. Lagos-Quintana M et al, *Science* 294,853-858 (2001).
46. Esquela-Kerscher A and Slack F J, *Nat Rev Cancer* 6, 259-269 (2006)
47. Mitchell P S et al, *Proc Natl Acad Sci USA* 105 10513-10518 (2008).
48. Bloomston M et al, *JAMA* 297, 1901-1908 (2007).
49. Lee E J et al *Int J Cancer,* vol. 120, 1046-1054, (2007).
50. Tibshirani R, *BMC Bioinformatics* 7, 106 (2006).
51. Kim S et al, *Comput Syst Bioinformatics Conf* 6, 169-179 (2007).
52. Nasser S et al in Genomic Signal Processing and Statistics, 2009, GENSiPS 2009. IEEE International Workshop pp. 1-4, (2009).
53. Vandesompele J et al, *Genome Biol* 3, research0034.1-research0034.11 (2002).
54. Storey J D, *Journal of the Royal Statistical Society,* Series B, 479-498 (2002).
55. Tusher V G et al, *Proc Nall Acad Sci USA,* 98, 5116-5121, (2001).
56. Seo J and Shneiderman B, IEEE Computer 35, 80-86 (2002).

SEQUENCE IDENTIFIERS

SEQ ID NO. 1—hsa-miR-328
SEQ ID NO. 2—hsa-miR-330-3p
SEQ ID NO. 3—hsa-miR-329-1-pre
SEQ ID NO. 4—hsa-miR-326-pre
SEQ ID NO. 5—hsa-miR-495-pre
SEQ ID NO. 6—hsa-miR-500*
SEQ ID NO. 7—hsa-miR-326
SEQ ID NO. 8—hsa-miR-370
SEQ ID NO. 9—hsa-miR-218
SEQ ID NO. 10—hsa-miR-122a
SEQ ID NO. 11—hsa-miR-325
SEQ ID NO. 12—hsa-miR-489-pre
SEQ ID NO. 13—hsa-miR-599
SEQ ID NO. 14—hsa-miR-329-2-pre
SEQ ID NO. 15—hsa-miR-346
SEQ ID NO. 16—hsa-miR-650-pre
SEQ ID NO. 17—hsa-miR-92a
SEQ ID NO. 18—hsa-miR-193-pre
SEQ ID NO. 19—hsa-miR-103

We claim:

1. A method of classifying a subject as having an increased risk of having non-small cell lung cancer that is likely to metastasize to the brain of the subject, the method comprising the steps of:
    obtaining a sample from the subject;
    isolating RNA from the sample;
    adding a first reagent capable of specific binding to a marker including a sequence selected from the group consisting of SEQ ID NO. 1 and SEQ ID NO. 2 to a mixture comprising the RNA;
    subjecting the mixture to conditions that allow detection of the binding of the first reagent to the marker;
    assessing an expression level of the marker in the sample by determining a level of binding of the first reagent to the marker in the sample;
    classifying the subject as having an increased risk of having non-small cell lung cancer that is likely to metastasize to the brain of the subject upon detection of an increased expression level of the marker in the sample; and
    treating the subject with the increased risk of having non-small cell lung cancer that is likely to metastasize to the brain with a prophylactic therapy.

2. The method of claim 1 wherein the first reagent comprises a first oligonucleotide.

3. The method of claim 2 wherein the first oligonucleotide comprises a stem-loop oligonucleotide.

4. The method of claim 2 further comprising adding reverse transcriptase to the mixture and wherein the conditions comprise the formation of a reverse transcription product comprising the marker.

5. The method of claim 4 further comprising adding a second oligonucleotide and a third oligonucleotide to the mixture, wherein the second oligonucleotide and the third oligonucleotide each bind to opposite strands of the reverse transcription product and wherein the conditions comprise nucleic acid amplification.

6. The method of claim 5 wherein the second oligonucleotide is capable of binding to the 5'→3' strand of the cDNA template.

7. The method of claim 5 further comprising adding a fourth oligonucleotide to the mixture wherein the fourth oligonucleotide binds to the reverse transcription product between the sequences to which the second oligonucleotide and the third oligonucleotide are capable of binding.

8. The method of claim 7 wherein the fourth nucleic acid comprises a fluorescent label selected from the group consisting of FAM, dR110, 5-FAM, 6FAM, dR6G, JOE, HEX, VIC, TET, dTAMRA, TAMRA, NED, dROX, PET, BHQ, Gold540, and LIZ.

9. The method of claim 4 wherein the conditions comprise DNA sequencing and the first reagent is affixed to a substrate.

10. The method of claim 1 further comprising collecting the sample from the subject, the sample comprising serum and/or a biopsy.

* * * * *

SEQUENCE LISTING

```
<160> NUMBER OF SEQ ID NOS: 19

<210> SEQ ID NO 1
<211> LENGTH: 22
<212> TYPE: RNA
<213> ORGANISM: Homo sapiens

<400> SEQUENCE: 1
cuggcccucu cugcccuucc gu                                             22

<210> SEQ ID NO 2
<211> LENGTH: 23
<212> TYPE: RNA
<213> ORGANISM: Homo sapiens

<400> SEQUENCE: 2
gcaaagcaca cggccugcag aga                                            23

<210> SEQ ID NO 3
<211> LENGTH: 80
<212> TYPE: RNA
```

<213> ORGANISM: Homo sapiens

<400> SEQUENCE: 3
gguaccugaa gagagguuuu cugguuuucu guuucuuuaa ugaggacgaa acacaccugg    60
uuaaccucuu uuccaguauc                                               80

<210> SEQ ID NO 4
<211> LENGTH: 95
<212> TYPE: RNA
<213> ORGANISM: Homo sapiens

<400> SEQUENCE: 4
cucaucuguc uguugggcug gaggcagggc cuuugugaag gcgggguggug cucagaucgc    60 cucugggccc uuccuccagc cccgaggcgg auuca                               95

<210> SEQ ID NO 5
<211> LENGTH: 82
<212> TYPE: RNA
<213> ORGANISM: Homo sapiens

<400> SEQUENCE: 5
ugguaccuga aaagaaguug cccauguuau uuucgcuuua uaugugacga aacaaacaug    60
gugcacuucu uuuucgguau ca                                             82

<210> SEQ ID NO 6
<211> LENGTH: 22
<212> TYPE: RNA
<213> ORGANISM: Homo sapiens

<400> SEQUENCE: 6
augcaccugg gcaaggauuc ug                                             22

<210> SEQ ID NO 7
<211> LENGTH: 20
<212> TYPE: RNA
<213> ORGANISM: Homo sapiens

<400> SEQUENCE: 7
ccucugggcc cuuccuccag                                                20

<210> SEQ ID NO 8
<211> LENGTH: 22
<212> TYPE: RNA
<213> ORGANISM: Homo sapiens

<400> SEQUENCE: 8
gccugcuggg guggaaccug gu                                             22

<210> SEQ ID NO 9
<211> LENGTH: 21
<212> TYPE: RNA
<213> ORGANISM: Homo sapiens

<400> SEQUENCE: 9
uugugcuuga ucuaaccaug u                                              21

<210> SEQ ID NO 10
<211> LENGTH: 22
<212> TYPE: RNA
<213> ORGANISM: Homo sapiens

<400> SEQUENCE: 10

-continued aacgccauua ucacacuaaa ua                                              22

<210> SEQ ID NO 11
<211> LENGTH: 23
<212> TYPE: RNA
<213> ORGANISM: Homo sapiens

<400> SEQUENCE: 11
ccuaguaggu guccaguaag ugu                                             23

<210> SEQ ID NO 12
<211> LENGTH: 84
<212> TYPE: RNA
<213> ORGANISM: Homo sapiens

<400> SEQUENCE: 12
guggcagcuu gguggucgua ugugugacgc cauuuacuug aaccuuuagg agugacauca    60
cauauacggc agcuaaacug cuac                                            84

<210> SEQ ID NO 13
<211> LENGTH: 20
<212> TYPE: RNA
<213> ORGANISM: Homo sapiens

<400> SEQUENCE: 13
guugugucag uuuaucaaac                                                 20

<210> SEQ ID NO 14
<211> LENGTH: 84
<212> TYPE: RNA
<213> ORGANISM: Homo sapiens

<400> SEQUENCE: 14
gugguaccug aagagagguu uucuggguuu cuguuucuuu auugaggacg aaacacaccu    60
gguuaaccuc uuuuccagua ucaa                                            84

<210> SEQ ID NO 15
<211> LENGTH: 23
<212> TYPE: RNA
<213> ORGANISM: Homo sapiens

<400> SEQUENCE: 15
ugucugcccg caugccugcc ucu                                             23

<210> SEQ ID NO 16
<211> LENGTH: 96
<212> TYPE: RNA
<213> ORGANISM: Homo sapiens

<400> SEQUENCE: 16
cagugcuggg gucucaggag gcagcgcucu caggacguca ccaccauggc cugggcucug    60
cuccuccuca cccuccucac ucagggcaca ggugau                               96

<210> SEQ ID NO 17
<211> LENGTH: 22
<212> TYPE: RNA
<213> ORGANISM: Homo sapiens

<400> SEQUENCE: 17
uauugcacuu gucccggccu gu                                              22

```
<210> SEQ ID NO 18
<211> LENGTH: 88
<212> TYPE: RNA
<213> ORGANISM: Homo sapiens

<400> SEQUENCE: 18
cgaggauggg agcugagggc ugggucuuug cgggcgagau gagggugucg gaucaacugg        60
ccuacaaagu cccaguucuc ggcccccg                                          88

<210> SEQ ID NO 19
<211> LENGTH: 23
<212> TYPE: RNA
<213> ORGANISM: Homo sapiens

<400> SEQUENCE: 19
agcagcauug uacagggcua uga                                               23
```